(12) United States Patent  
Soubeiran

(10) Patent No.: US 8,137,349 B2
(45) Date of Patent: Mar. 20, 2012

(54) INTRABODY DISTRACTION DEVICE WITH A SCREW WORKING IN TRACTION

(76) Inventor: Arnaud Soubeiran, Paris (FR)

( * ) Notice: Subject to any disclaimer, the term of this patent is extended or adjusted under 35 U.S.C. 154(b) by 486 days.

(21) Appl. No.: 12/304,195

(22) PCT Filed: Jun. 8, 2007

(86) PCT No.: PCT/FR2007/000950
§ 371 (c)(1),
(2), (4) Date: Dec. 10, 2008

(87) PCT Pub. No.: WO2007/144489
PCT Pub. Date: Dec. 21, 2007

(65) Prior Publication Data
US 2009/0254088 A1    Oct. 8, 2009

(30) Foreign Application Priority Data
Jun. 13, 2006 (FR) ...................................... 06 05236

(51) Int. Cl.
*A61B 17/22* (2006.01)
(52) U.S. Cl. ................. 606/63; 606/67; 606/68
(58) Field of Classification Search .............. 606/62–68, 606/320, 325–326, 329; 623/23.23
See application file for complete search history.

(56) References Cited

U.S. PATENT DOCUMENTS

| | | | | |
|---|---|---|---|---|
| 2,672,861 A * | 3/1954 | Jonas et al. | | 606/63 |
| 5,112,333 A * | 5/1992 | Fixel | | 606/62 |
| 5,263,955 A * | 11/1993 | Baumgart et al. | | 606/63 |
| 5,350,379 A * | 9/1994 | Spievack | | 606/63 |
| 5,534,004 A * | 7/1996 | Santangelo | | 606/68 |
| 5,704,939 A * | 1/1998 | Justin | | 606/63 |
| 6,336,929 B1 * | 1/2002 | Justin | | 606/63 |
| 6,796,984 B2 * | 9/2004 | Soubeiran | | 606/300 |
| 6,849,076 B2 * | 2/2005 | Blunn et al. | | 606/105 |
| 7,481,841 B2 * | 1/2009 | Hazebrouck et al. | | 623/18.12 |
| 7,559,951 B2 * | 7/2009 | DiSilvestro et al. | | 623/23.47 |
| 2005/0246034 A1 * | 11/2005 | Soubeiran | | 623/23.45 |
| 2005/0261779 A1 | 11/2005 | Meyer | | |
| 2010/0049204 A1 | 2/2010 | Soubeiran | | |
| 2010/0280519 A1 | 11/2010 | Soubeiran | | |

FOREIGN PATENT DOCUMENTS

| | | |
|---|---|---|
| DE | 85 15 687 U1 | 10/1985 |
| WO | 99/51160 A1 | 10/1999 |
| WO | 01/78614 A1 | 10/2001 |
| WO | 2004/019796 A1 | 3/2004 |

* cited by examiner

*Primary Examiner* — Eduardo C Robert
*Assistant Examiner* — Steven Cotroneo
(74) *Attorney, Agent, or Firm* — Scott E. Kamholz; Foley Hoag LLP

(57) ABSTRACT

An intra-corporal expandable device incorporating a screw operating under traction. A first elongated part (1) receives a second telescopic part (2). Each of these parts comprises links (61), (62) to the organism at a first end (11), (21) and is linked to a rod (3) comprising at least one thread at a second end (12) and (22). The rotation of the rod (3) controlled by means (4) causes a relative displacement of the two parts (1) and (2). The rod (3) is thus assembled between two ends (12) and (22) which come closer when the device is elongated, the length of the loaded rod (7) is reduced when the device is elongated and the length of loaded rod (7) operates only under traction. The device according to the invention is intended in particular for the production of osseous lengthening nails and growth prostheses.

15 Claims, 1 Drawing Sheet

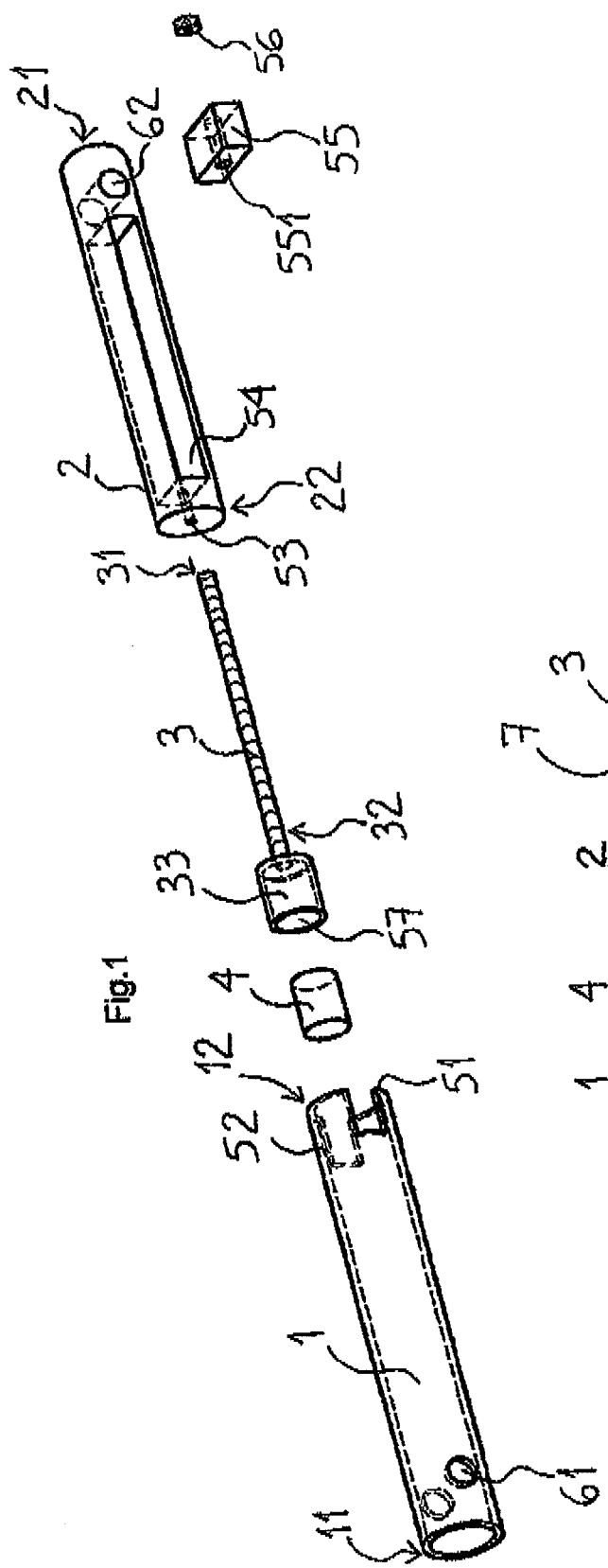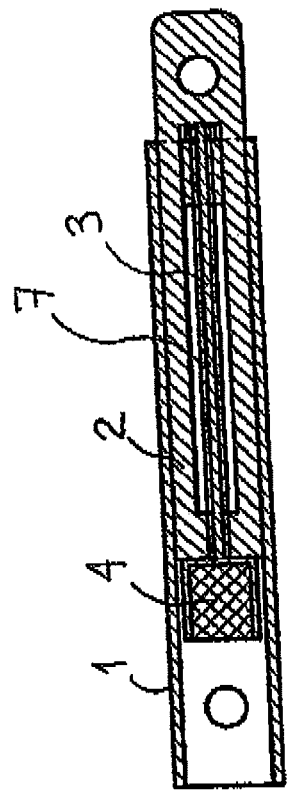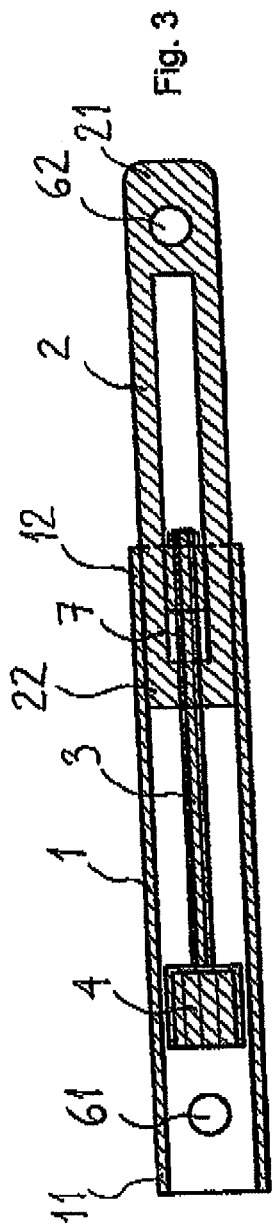

_US 8,137,349 B2_

INTRABODY DISTRACTION DEVICE WITH A SCREW WORKING IN TRACTION

FIELD

The present invention concerns intra-corporal expandable devices, such as bone lengthening nails, bone transport nails, spinal distraction rods or growth prostheses.

BACKGROUND

Several intra-corporal expandable devices including, notably, those described in documents U.S. Pat. No. 3,976,060, Proc Inst Mech Eng [H]. 1989; 203(2): 97-102., WO 01/78614, DE 85 15 687 U1 or U.S. Pat. No. 6,336,929 include a first elongated part, a second part assembled telescopically relative to the said first part, first links to the organism at a first end of the said first part, second links to the organism at a first end of the said second part, a rod with at least one thread, the rotation of which causes displacement of the second part relative to the said first part, means for controlling the rotation of the said rod and links between these components. However, in all these known devices the said rod is assembled between the said first end of the said first part, and the second end of the said second part opposite the said first end of the said second part. The said rod is thus assembled between two ends which move apart when the device is elongated, the loaded rod length increases when the device is elongated and the loaded rod length operates under compression when the device is elongated. As a consequence, the length of the elongation is limited by the buckling height of the said rod under the applied load, the volume devoted in the said device to the said rod and to the tapping with which it cooperates which does not contribute to the robustness, notably under deflection, of the said devices, is substantial and, above all, the torque required to rotate the said rod is also substantial, which determines the dimensioning of the means to control the rotation of the said rod accordingly, and restricts usage in practice of certain means which are simple and reliable but of limited power, such as direct magnetic transmission without amplification between two permanent magnets, for example as described in document U.S. Pat. No. 6,336,929.

SUMMARY

The present invention proposes to remedy these disadvantages. Indeed, in the intra-corporal expandable device according to the present invention which comprises a first elongated part, a second part assembled telescopically relative to the said first part, first links to the organism at a first end of the said first part, second links to the organism at a first end of the said second part, a rod with at least one thread, the rotation of which leads to the displacement of the said second part relative to the said first part, means for controlling the rotation of the said rod and links between these components, the said rod is assembled between two ends which come closer when the said device is elongated, the second end of the said first part opposite the said first end of the said first part and the second end of the said second part opposite the said first end of the said second part.

Thus the loaded rod length is reduced when the device is elongated and the loaded rod length operates under traction when the device is elongated.

The links between the said rod and the said second end of the said first part and the links between the said rod and the said second end of the said second part which may comprise, respectively:

a pivot and a tapping,
a tapping and a pivot,
a first tapping in a first direction and a second tapping in the direction opposite the said first direction; in this case the said rod contains a first thread able to cooperate with the said first tapping at one end, and a second thread able to cooperate with the said second tapping at the other end.

Moreover, according to the present invention, the said means to control the rotation of the said rod can be of all types, but preferentially consist of a driven permanent magnet assembled coupled with the said rod so that its magnetisation direction is roughly perpendicular to the axis of rotation of the said rod and, outside the organism, of a magnetic driving field source rotating roughly around the axis of the said rod. Advantageously the said driven permanent magnet is a neodymium magnet able to tolerate the sterilisation temperatures of the said intra-corporal expandable device according to the present invention and the said magnetic driving field source rotating outside the organism is at least one neodymium magnet which is rotated roughly around the axis of the said rod, whilst keeping one of its poles constantly turned towards it. Equally advantageously, the speed of rotation of the said magnetic field will be able to be less than one rotation per minute. The diameter of the said rod will, for its part, advantageously be less than 4 mm.

BRIEF DESCRIPTION OF THE DRAWINGS

The invention, its operation and its applications will be better understood, and others of its characteristics and advantages will be revealed, in the course of the following description made on sight of the illustrations appended for illustrative purposes, but by no means on a restrictive basis, in which:

FIGS. 1 to 3 represent a preferred embodiment of the device according to the invention, which is particularly useful for limb lengthening. FIG. 1 is an exploded perspective view of this embodiment, with the hidden lines shown as dotted. FIG. 2 is a section view of it, the section passing through the axis of the said rod containing at least one thread in the shortest position of the said embodiment. FIG. 3 is a section view, the section again passing through the axis of the said rod, where the said embodiment is represented almost fully elongated.

It is specified that, in these figures, the same references designate the same elements, whatever the figure in which they appear, and however these elements are represented. Similarly, if elements are not specifically referenced in one of the figures, the reference can easily be found by referring to another figure. In all the figures the dimensions and proportions have been altered when this could facilitate understanding. In addition, when, according to the definition of the invention, the object of the invention comprises "at least one" element with a given function, the described embodiment may contain several of these elements.

DESCRIPTION OF ILLUSTRATIVE EMBODIMENTS

A preferred embodiment of the device represented in FIGS. 1 to 3 includes:

a first roughly tubular elongated part 1 which contains, at a first end 11, links to the organism, consisting for example of a first hole 61 roughly perpendicular to the axis of the said first part 1 and intended to receive a screw, which is not represented, and at the second end 12, opposite the said first end 11, two longitudinal and diametrically opposite notches 51, 52. The said first end 11 can also contain unrepresented means for gripping, such as a thread and a slot, for example, the said device to facilitate its surgical implantation, in general in the medullar cavity of a long bone or along or as an extension of all or part of a long or flat bone, and also its explantation.

a second, roughly cylindrical, part 2 the outer diameter of which is roughly equal to the inner diameter of the said first part 1, with which it cooperates telescopically and which contains, at a first end 21, links to the organism, consisting for example of a second 62 hole roughly perpendicular to the axis of the second part 2 and intended to receive a screw, which is not represented, and at the second end 22, opposite the said first end 21, and which still remains in contact with the said first part 1, a tapping 53 roughly along the axis of the said second part 2. Between the two ends, a longitudinal groove 54 opens diametrically out on either side of the said second part 2. The width of the said groove 54 is roughly equal to the width of the said notches 51, 52 made in the said second end 12 of the said first part 1 and the said tapping 53 opening on to the said groove 54, and having a diameter appreciably less than the width of the said groove 54.

a rod 3 which contains at a first end 31 a thread of diameter and pitch equal to those of the tapping 53 of the said second part 2, with which the said thread cooperates, links between these components consisting:

of a roughly parallelepipedal supporting strip 55 able to be fit in the said two notches 51, 52 made in the second end 12 of the said first part 1 in order to form a bridge between them. The said supporting strip 55 also contains, roughly in its middle, a hole 551 in which the said first end 31 of the said rod 3 can slide and rotate freely, of a supporting nut 56 which can be screwed on to the said first end 31 of the rod 3.

The said supporting strip 55 and the said supporting nut 56 form a pivot between the said rod 3 and the said second end 12 of the said first part 1.

In this preferred embodiment of the invention, the said means to control the rotation of the said rod 3 consist;

of a cylindrical driven permanent magnet 4 with diametrical magnetisation coaxially coupled with the said rod 3, for example by gluing using a silicone glue which is easily tolerated by the organism in a cylindrical cavity 57 coaxial with the axis of the said rod 3 and made in a cylindrical bulge 33 coupled with the second end 32 opposite the said first end 31 of the said rod 3.

of a magnetic driving field source rotating around the axis of the said rod 3 and unrepresented on FIGS. 1 to 3 positioned outside the organism.

It can be noted that the said means for controlling the rotation of the said rod 3 can also consist of any other means known to the skilled man in the art such as an electric motor with or without gear reducer, and a current source inside or outside the organism, or a permanent magnet with a gear reducer and a rotating magnetic field source outside the organism, or a free-wheeling system able to transform the torques which may exist between the said first part 1 and the said second part 2 of the device when the patient rotates in a single direction of the said rod 3. These said means may be able to drive the said rod 3 in one direction only or in both directions, according to requirements.

The various components of the said preferred embodiment of the device represented in FIGS. 1 to 3 are assembled as follows: the said first end 31 of the said rod 3 is screwed into the said tapping 53 of the said second part 2. As soon as the said first end 31 of the said rod 3 protrudes sufficiently beyond the said second part 2 in the said groove 54, the said supporting strip 55 is slid into the said groove 54 and then slipped on, through its hole 551, to the said first end 31 of the said rod 3. The supporting nut 56 is then screwed on to the said first end 31 of the said rod 3 which protrudes beyond the said supporting strip 55 in the said groove 54 and locked definitively on the said rod 3, for example using a laser weld at the end, or by crushing through the said groove 54, causing an ovalisation of at least part of the said nut 56 and of the part of the said first end 31 of the said rod 3 which is located there. The system constituted in this manner is introduced into the said second end 12 of the said first part 1, the said second end 32 of the said rod 3 and the said second end 22 of the said second part 2 firstly, until the said supporting strip 55 comes up against the said notches 51, 52 of the said second end 12 of the said first part 1. It is then possible to couple definitively the said supporting strip 55 and the said first part 1, for example by means of a laser weld. The assembly of this preferred embodiment of the invention is thus completed.

All the parts are made from a mechanically resistant material which is well tolerated by the organism such as 316L recast in a vacuum, certain titanium alloys, or high-resistance chrome- and cobalt-based alloys. Advantageously the surfaces of the parts, and particularly of the said rod 3, are treated to limit friction and possible wear and tear. Treatments based on amorphous diamond-like carbon or tungsten disulphide are preferred. The combination of the small diameter of the said rod 3, allowed by its assembly and its operation under traction, and of the low friction coefficient obtained due to the said surface treatments, allows the said rod 3 to be driven by a modest torque with regard to the applied load, and compared to what it would be if the said rod 3 had been dimensioned for operation under compression. The diameter of the said rod 3 is commonly between one and three millimeters and does not exceed four millimeters for an adult patient prosthesis, for example.

If the rod 3 has been designed with sufficient length, the maximum length variation potential of the said preferred embodiment of the said device according to the invention is roughly equal to the length of the said groove 54 of the said second part 2 minus the length necessary to accommodate the said supporting strip 55 and the said supporting nut 56; otherwise it is the length of the said rod 3 which limits the said potential.

The operation of this preferred embodiment of the invention is clear: in the presence of a magnetic driving field perpendicular to the axis of the said rod 3 and rotating around this axis, the said cylindrical driven permanent magnet 4 coupled coaxially with the said rod 3 tends to become oriented in the said magnetic driving field applying a torque to the said rod 3 and causing it to rotate in the rotational direction of the said magnetic driving field if this torque is greater than the load torque of the said rod 3 under the load applied to it at the time when the magnetic driving field is activated. The said rotation of the said rod 3 is displaced in one direction or the other of the said second part 2 relative to the said first part 1, depending on the thread direction of the said rod 3 and said tapping 53, and thus the device according to the invention is elongated or shortened. The said second end 12 of the said first part 1 and the said second end 22 of the said second part 2 come closer when the device is elongated. The loaded length 7 of the said rod 3 is reduced when the device is elongated and the said loaded length 7 is under traction when the device is elongated.

Moreover, still referring to the said preferred embodiment of the device according to the invention represented in FIGS. 1 to 3, it is impossible to apply compression to the said rod 3 since it then slides into the hole 551 of the said supporting strip 55, and the supporting nut 56 locks it only in the other direction, the other direction in which the rod 3 is subjected to traction.

The creation of a magnetic driving field favourable for rotating the said cylindrical driven permanent magnet 4 coupled coaxially to the said rod 3 and of the said rod 3 can be accomplished by any means, but preferentially by positioning outside the organism, at the height of the said driven permanent magnet 4 at least one other permanent driving magnet, one of the poles of which is directed towards the axis common to the said rod 3 and to the said driven permanent magnet 4. The combination of two permanent driving magnets positioned such that the south pole of one is facing the north pole of the other, and such that the said driven permanent magnet 4 and the part of the organism which surrounds the said device are positioned between the two will produce an even greater motor torque, and may be preferred.

It is clearly stipulated that the embodiment of the invention represented in FIGS. 1 to 3 is a preferred embodiment, but other embodiments conforming to the definition of the invention exist and will be able to be produced by the man skilled in the art. In particular the said rod 3 may be off-centre relative to the said first 1 and second 2 parts and the said first 1 and second 2 parts may have geometries other than a tube and a cylinder respectively, and each consist of several parts assembled by any means. Moreover, the said first end 21 of the said second part 2 may be on the side of the said first end 11 of the said first part 1 and the said second end 22 of the said second part 2 on the side of the second end 12 of the said first part 1, unlike in the preferred embodiment represented in FIGS. 1 to 3. In this second configuration, the said second part 2 is constantly in full contact with the said first part 1 and grooves are made in the said first part 1 to allow linking to links to the organism contained by the said first end 21 of the said second part 2 along the entire elongation course of the said device.

Possibilities for Industrial Application

The present invention is particularly useful for the construction of any type of intra-corporal expandable device, and particularly medullar lengthening nails and long bones growth prostheses.

The invention claimed is:

1. An intra-corporal expandable device comprising a first elongated part (1), a second part (2) mounted telescopically relative to the said first part (1), first links (61) for attaching to an organism at a first end (11) of the said first part (1), second links (62) for attaching to the organism at a first end (21) of the said second part (2), a rod (3) with at least one thread, the rotation of which leads to the displacement of the said second part (2) relative to the said first part (1), means (4) for controlling the rotation of the said rod (3) and connections between these components wherein the said rod (3) is mounted between two ends which come closer when the said device is elongated, the second end (12) of the said first part (1) opposite the said first end (11) of the said first part (1) and the second end (22) of the said second part (2) opposite the said first end (21) of the said second part (2), so that the rod (3) is under traction when the device is in operation.

2. An intra-corporal expandable device according to claim 1, wherein the connection between the said rod (3) and the said second end (12) of the said first part (1) comprises a pivot (55), (56) and the connection between the said rod (3) and the said second end (22) of the said second part (2) comprises a tapping (53) able to cooperate with the said rod (3).

3. An intra-corporal expandable device according to claim 1, wherein the connection between the said rod (3) and the said second end (12) of the said first part (1) comprises a tapping able to cooperate with the said rod (3) and the connection between the said rod (3) and the said second end (22) of the said second part (2) comprises a pivot.

4. An intra-corporal expandable device according to claim 1 wherein the connection between the said rod (3) and the said second end (12) of the said first part (1) comprises a first tapping in a first direction and the connection between the said rod (3) and the said second end (22) of the said second part (2) comprises a second tapping in the direction opposite to the said first direction and that the said rod (3) comprises a first thread able to cooperate with the said first tapping at one end, and a second thread able to cooperate with the said second tapping at the other end.

5. An intra-corporal expandable device according to claim 1 wherein the said means to control the rotation of the said rod (3) comprises at least one permanent magnet (4) rigidly mounted to the said rod (3) such that its magnetisation direction is substantially perpendicular to the axis of rotation of the said rod (3) and a magnetic field source rotating substantially around the axis of the said rod (3).

6. An intra-corporal expandable device according to claim 5 wherein the speed of rotation of the said magnetic field produced by the said rotating magnetic field source is less than one revolution per minute.

7. An intra-corporal expandable device according to claim 1 wherein the diameter of the said rod (3) is less than four millimeters.

8. The intra-corporal expandable device of claim 1, wherein a loaded length (7) of the rod (3) is reduced as the device is elongated.

9. A distraction device, comprising:
a first elongated part having a first end and a second end, the first end opposite the second end;
a second part mounted telescopically with respect to the first part, the second part having a first end and a second end, the first end of the second part being opposite the second end of the second part, the second part oriented such that as the second part telescopes outward from the first part, the second end of the second part moves toward the second end of the first part;
a first connector at a first end of the first part, for connecting to a body;
a second connector at a first end of the second part, for connecting to the body;
a rod comprising a first thread and mounted between the second end of the first part and the second end of the second part, the rotation of which rod causes displacement of the second part relative to the first part; and
a rotation controller for controlling rotation of the rod;
wherein the rod is in tension when the device is in operation.

10. The distraction device of claim 9, wherein:
the rod is connected to the second end of the first part by a pivot; and
the second end of the second part comprises a tapping that cooperates with the first thread of the rod;
so that as the rod rotates:
the rod does not move relative to the first part; and
the second part telescopes outward from the first part.

11. The distraction device of claim 9, wherein:
the rod is connected to the second end of the second part by a pivot; and the second end of the first part comprises a tapping that cooperates with the first thread of the rod;

so that as the rod rotates, the rod and the second part telescope outward from the first part.

12. The distraction device of claim 9, wherein:

the second end of the first part comprises a first tapping in a first direction that cooperates with the first thread of the rod;

the second end of the second part comprises a second tapping in a second direction opposite the first direction;

the first thread of the rod cooperates with the first tapping; and the rod further comprises a second thread that cooperates with the second tapping.

13. The distraction device of claim 9, wherein the rotation controller comprises a permanent magnet rigidly mounted to the rod such that its magnetisation direction is substantially perpendicular to the rod's axis of rotation, such that rotation of a magnetic field source substantially around the rod's axis of rotation causes rotation of the rod.

14. The distraction device of claim 9, wherein the rod has a diameter of less than four millimeters.

15. The distraction device of claim 9, wherein a loaded length of the rod is shortened as the second part telescopes outward from the first part.

* * * * *